United States Patent [19]

Nakagawa

[11] Patent Number: 5,378,344
[45] Date of Patent: Jan. 3, 1995

[54] ION SENSOR

[75] Inventor: Tohru Nakagawa, Kusatsu, Japan

[73] Assignee: Matsushita Electric Industrial Co., Ltd., Osaka, Japan

[21] Appl. No.: 43,550

[22] Filed: Apr. 7, 1993

[30] Foreign Application Priority Data

May 18, 1992 [JP] Japan .................. 4-124574

[51] Int. Cl.⁶ .............................. G01N 27/26
[52] U.S. Cl. ..................... 204/418; 204/403; 204/415
[58] Field of Search ............... 204/403, 418, 419, 416, 204/153.12, 153.17, 415

[56] References Cited

U.S. PATENT DOCUMENTS

| | | | |
|---|---|---|---|
| 4,721,677 | 1/1988 | Clark, Jr. | 204/415 |
| 4,795,542 | 1/1989 | Ross et al. | 204/415 |
| 4,886,740 | 12/1989 | Vadgama | 204/153.12 |
| 4,964,972 | 10/1990 | Sagiv et al. | 204/418 |
| 4,999,284 | 3/1991 | Ward et al. | 204/403 |

OTHER PUBLICATIONS

Jonathan A. Stamford et al., "Striatal Dopamine Uptake in the Rat: In Vivo Analysis by Fast Cyclic Voltammetry," *Neuroscience Letter*, 51, (1984) 133–138.

J. Miller et al., "Electrochemical, Pharmacological and Electrophysiological Evidence of Rapid Dopamine Release and Removal in the Rat Caudate Nucleus," *European Journal of Pharmacology*, 109 (1985) 341–348.

Primary Examiner—John Niebling
Assistant Examiner—Bruce F. Bell
Attorney, Agent, or Firm—Fish & Richardson

[57] ABSTRACT

Disclosed is an ion sensor with its electrode covered with a water-repelling organic chemically adsorbed film, which is formed with at least one hole permitting the passage of ions and preventing the passage of biopolymers, thereby accurately measuring ion concentrations over a long period. In forming a silane-based chemically adsorbed monomolecular film on the surface of the electrode, a hole dozens of angstroms in diameter is formed on an organic thin film by physically adsorbing the mask compound and then washing it away. This ion sensor can prevent the passage of macromolecules such as proteins in a living body. The sensor can also be used in a solution containing numerous impurities, and can be applied for monitoring activities in the body by implanting it in a body.

10 Claims, 5 Drawing Sheets

ION SENSOR

FIELD OF THE INVENTION

The invention relates to an ion sensor having its electrode covered with a water-repelling organic chemically adsorbed film, wherein at least one hole permitting the passage of ions and preventing the passage of biopolymers is formed in the organic chemically adsorbed film, thereby permitting accurate measurements of ion density over a long period.

BACKGROUND OF THE INVENTION

The invention provides an ion sensor, which can be used even in a solution containing numerous impurities. More specifically, the invention provides an ion sensor, implanted in a living body, capable of monitoring activities in the body.

When a particular ion in solution is oxidized or reduced by an electrode, an oxidation or reduction current flows to the electrode. The value of the electric current is generally correlated to ion concentration. Thus, this principle has been utilized for developing ion sensors in many fields. For example, since many neurotransmitters are oxidized or reduced by a platinum and carbon electrode, a particular nervous tract of the brain can be simply and easily examined by implanting these microelectrodes in the brain.

Ion sensors are excellent for observing ions in a solution immediately; however, they have the problem that they are incapable of providing reliable data when in a solution containing numerous impurities likely to stick to the surface of the electrode. Particularly, in measuring a neurotransmitter of a living body by using a conventional ion sensor, organic molecules in a body fluid such as proteins stick to its electrode, and the sensor becomes incapable of measuring the neurotransmitter. This has been a serious problem because a sensor which is implanted in the body cannot be frequently taken out and re-implanted into the body.

SUMMARY OF THE INVENTION

An objective of the invention is to provide an ion sensor which can be applied even in a solution containing numerous impurities.

In order to accomplish the above objective, the ion sensor of the invention comprises an electrode with its surface formed with a thin film by covalently bonding water-repelling chemical admolecules, wherein at least one hole permitting the passage of ions and preventing the passage of biopolymers is formed in the chemically adsorbed thin film.

It is preferable in this invention that the size of the hole preventing the passage of biopolymers is in the range of 0.5–50 nm$^2$.

It is preferable in this invention that the chemical admolecule is fixed to the electrode surface via covalent bonding containing siloxane groups (—SiO—).

It is preferable in this invention that the chemically adsorbed thin film is a monomolecular film.

It is preferable in this invention that the chemically adsorbed thin film is formed on an inorganic siloxane-based inner layer.

It is preferable in this invention that the thickness of the chemically adsorbed thin film is in range of 1–10 nm.

It is preferable in this invention that the molecule of the chemically adsorbed thin film contains a hydrocarbon or fluorocarbon group.

It is preferable in this invention that the electrode is at least one material selected from the group consisting of platinum, glassycarbon, silicon, gold and aluminum.

It is preferable in this invention that the procedures for manufacturing an ion sellsor comprise:

dipping and holding an electrode having hydrophilic groups on its surface ill a chemical adsorbent prepared by dissolving or dispersing chemical admolecules, containing water-repellent and chlorosilyl groups, and mask molecules with a physical adsorption property on their surfaces in a nonaqueous solution:

physically adsorbing the mask molecules to the electrode surface, thereby forming a chemically adsorbed film by a condensation reaction between the chemical admolecules and the chlorosilyl groups; and washing away the unreacted chemical admolecules and the mask molecules with a nonaqueous solution.

It is preferable in this invention that the mask molecule is at least one chosen from the group consisting of a carbocyanin and pyridinium compounds having molecular weight in a range of 500–1000.

According to the invention, impurities are not likely to stick to an electrode with its surface covered with a water-repelling organic chemically adsorbed thin film. Particularly, when using such a sensor in a living body, organic compound (organic polymers) such as proteins rarely stick to the electrode. Micromolecules such as ions can reach the electrode by passing through a hole on the scale of dozens of angstroms in diameter formed in the organic thin film; however, macromolecules such as protein can not penetrate the hole. Therefore, compared with the conventional microscopic electrode, the electrode of this invention has a superior reliability in the sense that it cannot be contaminated by impurities on a scale larger than dozens of angstroms in diameter.

In the above-noted composition, the size of the hole is in the range of 0.5–50 nm$^2$, thereby preventing the passage of biopolymers such as proteins while permitting the passage of micromolecules such as ions.

An organic chemically adsorbed thin film, which is bonded to an electrode surface via covalent bonds comprising siloxane groups (—SiO—), is not easily peeled off, thereby providing an ion sensor with superior biological adaptability, safety and endurance.

Moreover, the chemically adsorbed thin film is a monomolecular film with a uniform thickness.

It is also possible to increase the density of chemical admolecules by forming a chemically adsorbed thin film on an organic siloxane-based inner layer.

If the thickness of the chemically adsorbed thin film is in range of 1–10 nm, it is easy to measure ions in a living body.

A water-repelling property can be effectively demonstrated if hydrocarbon or fluorocarbon groups are contained in the molecules of the chemically adsorbed thin film.

In case that an electrode comprises at least one selected from the group consisting of platinum, glassycarbon, silicon, gold and aluminum, it is easy to form a chemically adsorbed thin film.

An ion sensor of the invention can be efficiently provided by the following procedures:

preparing a chemical adsorbent by dissolving or dispersing chemical admolecules containing water-repellent and chlorosilyl groups and mask molecules with a physical adsorption property in a nonaqueous solution;

dipping and holding an electrode having hydrophilic groups on its surface in the prepared chemical adsorbent, thereby physically adsorbing mask molecules to the electrode surface;

forming a chemically adsorbed film by a condensation reaction between hydrophilic groups on the electrode surface and the chlorosilyl groups of chemical admolecules;

washing away unreacted chemical admolecules and mask molecules with a nonaqueous solution.

The hole, permitting the passage of micromolecules such as ions and preventing the passage of biopolymers such as protein, is accurately formed when the mask molecule is at least one chosen from the group consisting of a carbocyanin and pyridinium compounds having molecular weights in a range of 500–1000.

DETAILED DESCRIPTION OF THE INVENTION

As examples of mask molecules of the invention, carbocyanin and pyridinium compounds or the like are shown in the following Formulas 1 or 2.

Formula 1

Formula 2 where $n_1$ represents 0, 1 and 2, $n_2$ represents 9 to 20 and $n_3$ represents 9 to 20. ($n_1=1$ and $n_2=n_3=18$ are preferable.)

In the case wherein $n_1=1$ and $n_2=n_3=17$, the compound is N,N'-dioctadecyloxacarbocyanine for Formula [1] and N,N'-dioctadecylthiacarbocyanine for Formula 2. In the case wherein $n_1=0$ and $n_2=n_3=17$, the compound N,N'-dioctadecylindocarbocyanine for Formula 1 and N,N'-dioctadecyl-4,4'bipyridinium for Formula 2.

The silane-based surface active agent comprising alkyl groups is a reagent which can be chemically adsorbed to an electrode substrate via siloxane coupling. Such an active agent includes a trichlorosilane-based chemical adsorbent, such as $CH_3(CH_2)_nSiCl_3$, a dichlorosilane-based chemical adsorbent, such as $CH_3(CH_2)_nCH_3SiCl_2CH_3$ and $CH_3(CH_2)_nSiCl_2C_2H_5$, or a monochlorosilane-based chemical adsorbent, such as $CH_3(CH_2)_nSiCl(CH_3)_2$ and $CH_3(CH_2)_nSiCl(C_2H_5)_2$ (where n represents 0–25. but most preferably 10–20). Among these examples, the trichlorosilane-based chemical adsorbent is preferred in that a siloxane coupling is formed on an electrode substrate surface and between adjacent molecules, thereby permitting the formation of a more firmly adsorbed film.

The silane-based surface active agent comprising fluoroalkyl groups can be a reagent which is chemically adsorbed to an electrode substrate via siloxane coupling, and such an agent include trichlorosilane-, monochlorosilane- or dichlorosilane-based chemical adsorbents.

Trichlorosilane-based chemical adsorbents include the following examples:

$CF_3(CF_2)_7(CH_2)_2SiCl_3$;
$CF_3CH_2O(CH_2)_{15}SiCl_3$;
$CF_3(CH_2)_2Si(CH_3)_2(CH_2)_{15}SICl_3$;
$CF_3(CF_2)_3(CH_2)_2Si(CH_3)_2(CH_2)_9SICl_3$;
$F(CF_2)_8(CH_2)_2Si(CH_3)_2(CH_2)_9SICl_3$;
$CF_3COO(CH_2)_{15}SICl_3$;
$CF_3(CF_2)_5(CH_2)_2SICl_3$.

Monochlorosilane- or dichlorosilane-based chemical adsorbents with lower-alkyl groups substituted are shown in the following examples:

$CF_3(CF_2)_7(CH_2)_2SiCl_n(CH_3)_{3-n}$;
$CF_3(CF_2)_7(CH_2)_2SiCl_n(C_2H_5)_{3-n}$;
$CF_3CH_2O(CH_2)_{15}SiCl_n(CH_3)_{3-n}$;
$CF_3CH_2O(CH_2)_{15}SiCl_n(C_2H_5)_{3-n}$;
$CF_3(CH_2)_2Si(CH_3)_2(CH_2)_{15}SiCl_n(CH_3)_{3-n}$;
$F(CF_2)_4(CH_2)_2Si(CH_3)_2(CH_2)_9SiCl_n(C_2H_5)_{3-n}$;
$F(CF_2)_8(CH_2)_2Si(CH_3)_2(CH_2)_9SiCl_n(CH_3)_{3-n}$;
$CF_3COO(CH_2)_{15}SiCl_n(CH_3)_{3-n}$;
$CF_3(CF_2)_5(CH_2)_2SiCl_n(CH_3)_{3-n}$ where n represents 1 or 2.

Among these examples, a trichlorosilane-based chemical adsorbent is preferred in that a siloxane coupling is formed on an electrode substrate surface and between adjacent molecules, thus permitting the formation of a more firmly adsorbed film.

In incorporating a vinyl group (C=C) or acethyl group (ethynyl group) in an alkyl or fluoroalkyl group portion, the formed chemically adsorbed film can be crosslinked by being irradiated with an electron beam of about $5\times10^6$ rads, thus further improving the firmness of the chemically adsorbed film. The chlorosilane-based surface active agents capable of use according to the invention are not limited to those in the form of a straight chain as noted above. It is possible to use agents with branched fluoroalkyl or hydrocarbon groups or those with silicons at one end substituted by fluoroalkyl or hydrocarbon groups (i.e., $R^2SiCl_3$, $R_3SiCl$, $R_1R_2SiCl_2$, $R_1R_2R_3SiCl$ or the like, where R, $R^1$, $R^2$ and $R^3$ represent fluoroalkyl or hydrocarbon groups). To increase the adsorption density, however, the straight chain form is preferred.

The nonaqueous solvent used to form a chemically adsorbed film comprising alkyl or fluoroalkyl groups on an electrode substrate via siloxane coupling may be any organic solvent so long as it does not have active hydrogen which can react with the chlorosilane-based surface active agent. Any of the solvents including fluorine-, hydrocarbon-, ether- and ester-based solvents can be a preferable organic solvent.

Examples of fluorine-based solvents are as follows:
1,1-dichloro,1-fluoroethane;
1,1-dichloro,2,2,2-trifluoroethane;
1,1-dichloro-2,2,3,3,3-pentafluoropropane;
1,3-dichloro,1,1,2,2,3-heptafluoropropane;
trifluoroalkylamine;
perfluorofuran and its fluoroalkyl derivative.
Hydrocarbon-based solvents include the following:
hexane; octane; hexadecane; cyclohexane; etc.
Ether-based solvents include the following:
dibutylether; dibenzylether; etc.
Ester-based solvents include the following:
methyl acetate; ethyl acetate; isopropyl acetate; amyl acetate; etc.

A single layer of a monomolecular chemically adsorbed film can be formed on an electrode substrate simply by following the procedures mentioned below:
preparing a solution by dissolving a chlorosilane-based surface active agent in a nonaqueous organic solvent mentioned above;
dipping and holding the electrode substrate in the solution, thereby promoting a dehydrochlorination reaction between the hydrophilic groups on the substrate surface and the chlorosilyl groups of the agent;
washing away the unreacted agent with a nonaqueous solvent; and
reacting the substrate with water.

As an electrode substrate used for the invention, any substrate with hydrophilic groups such as hydroxyl groups projecting from its surface may be used. However, platinum, glassycarbon, silicon, gold and aluminum are particularly excellent as electrode materials.

The invention is further described below by referring to the following practical embodiment.

Figure 2:
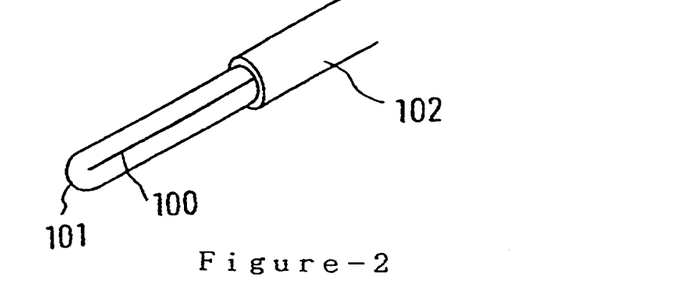
FIG. 2 is a view showing the process of manufacturing an electrode in an embodiment of the invention.
Figure 3:
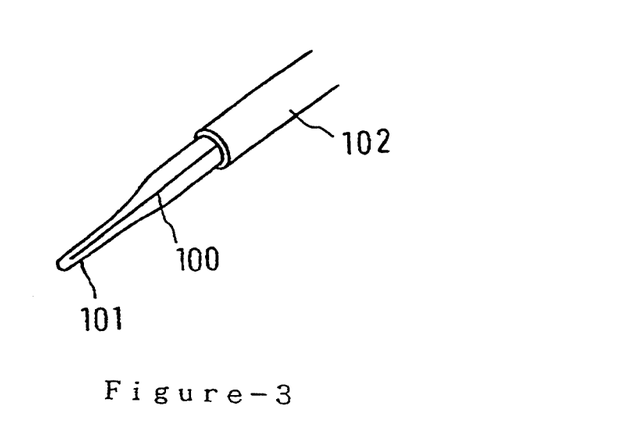
FIG. 3 is a view showing the process of manufacturing an electrode in an embodiment of the invention.
Figure 4:
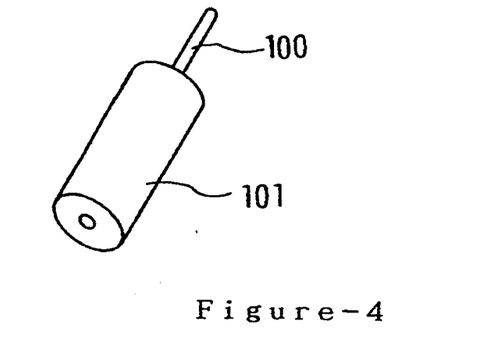
FIG. 4 is a view showing the process of manufacturing an electrode in an embodiment of the invention.
Figure 5:
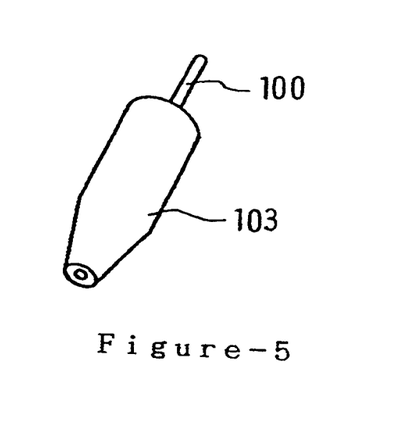
FIG. 5 is a view showing the process of manufacturing an electrode in an embodiment of the invention.

A platinum wire 100 several μm in diameter was inserted in a glass tube 101 of 1 mm inside diameter with one end closed. The open end of the tube was connected to a vacuum pump, and the inside of the tube was evacuated to a vacuum (FIG. 2). Glass tube 101 was melted by hearing the outside with a gas burner, and platinum wire 100 was inserted in the vacuum tube. Then, the end of the tube was ground with sand paper and diamond paste until platinum wire 100 emerged from the surface (FIG. 4). The end of the tube was again ground with emery paper (manufactured by Buehler Ltd.; commodity number Grit 600) and diamond paste, thereby tapering the end (FIG. 5).

The electrode manufactured in the above-noted procedures was dipped and held in a solution prepared by dissolving 30 mM/L octadecyl trichlorosilane (OTS) and 5 μM/L of the compound shown in Formula 3 below (mixed solution of n-hexadecane, chloroform and carbon tetrachloride at a volume ratio of 80:8:12) for two hours.

Formula 3

The unreacted material was washed away with a nonaqueous solution, in this case chloroform. The electrode was then washed and reacted with pure water.

Figure 1:
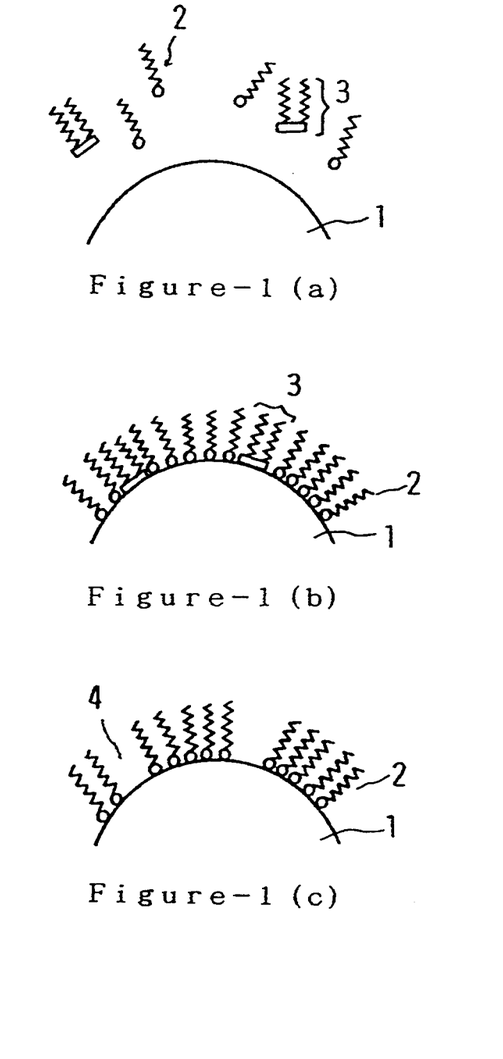
FIGS. 1(a)–1(c) are flow diagram showing the formation of an organic chemically adsorbed film in an embodiment of the invention.

By the above-noted treatments, OTS 2 was chemically bonded to platinum electrode 1 via siloxane coupling, and a compound 3 in Formula 3 was physically adsorbed to the electrode (FIG. 1-a and b). Only physically adsorbed compound 3 (Formula 3) was washed away with chloroform. After washing the electrode with water, the bond between each monomolecular film changed to siloxane bonds and a hole 4 was made on the spot where compound 3 existed. The film chemically adsorbed on the electrode surface is stable, and has holes at the molecular level (FIG. 1-c). In other words, the film has holes permitting the passage of ions while preventing the passage of biopolymers. The size of the hole can be easily controlled by changing the size of the mask molecules.

The procedures of covalent bonding between OTS and an electrode are more specifically described below.

Figure 6:
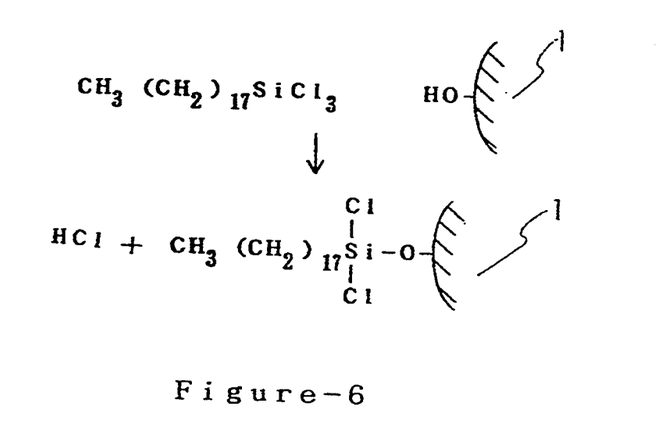
FIG. 6 is a view showing the process of octadecyl trichlorosilane being covalently bonded to an electrode surface in an embodiment of the invention.
Figure 7:
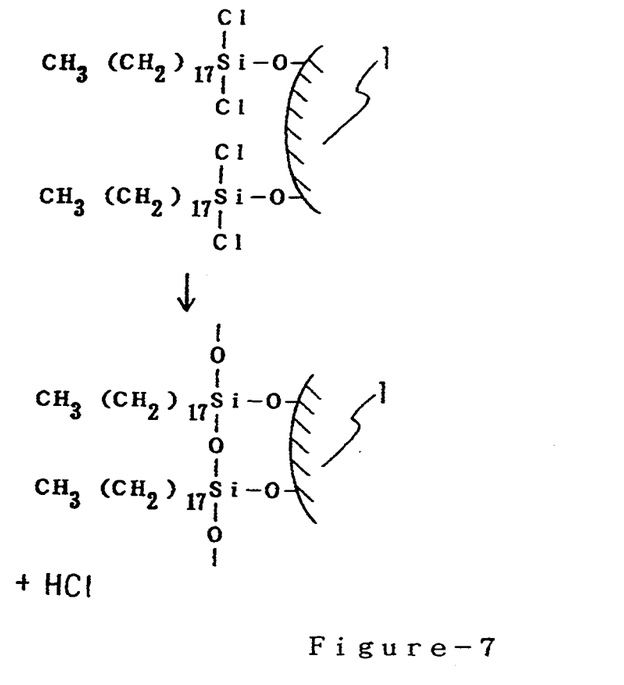
FIG. 7 is a view showing the process of OTS being bonded to each other via siloxane coupling in an embodiment of the invention.

After contacting the electrode surface with OTS, silanol bonds were formed by a dehydrochlorination reaction between the chlorosilyl groups of OTS and the hydroxyl groups on the surface (FIG. 6). The unreacted material was washed away with nonaqueous chloroform solution, and the electrode was washed with water, thereby substituting the remaining chlorosilyl groups with silanol groups. The electrode was then dried; as a result, the silanol groups were dehydrated and became siloxane bonds (FIG. 7).

The density of the holes in the OTS film on the electrode surface was estimated in the following ways:

Platinum was deposited on a glass substrate in a 1000 angstrom layer by vacuum deposition, providing an electrode. The electrode was dipped and held in a solution prepared by dissolving 30 mM/L OTS and 5 μM/L of the compound in Formula 3 (a mixed solution of n-hexadecane, chloroform and carbon tetrachloride at a volume ratio of 80:8:12) for two hours. After removing the substrate from the solution, the substrate, which gained a water-repelling property, repelled the solution, and only a monomolecular film covalently bonded or physically adsorbed to the substrate stayed on the substrate.

Figure 8:
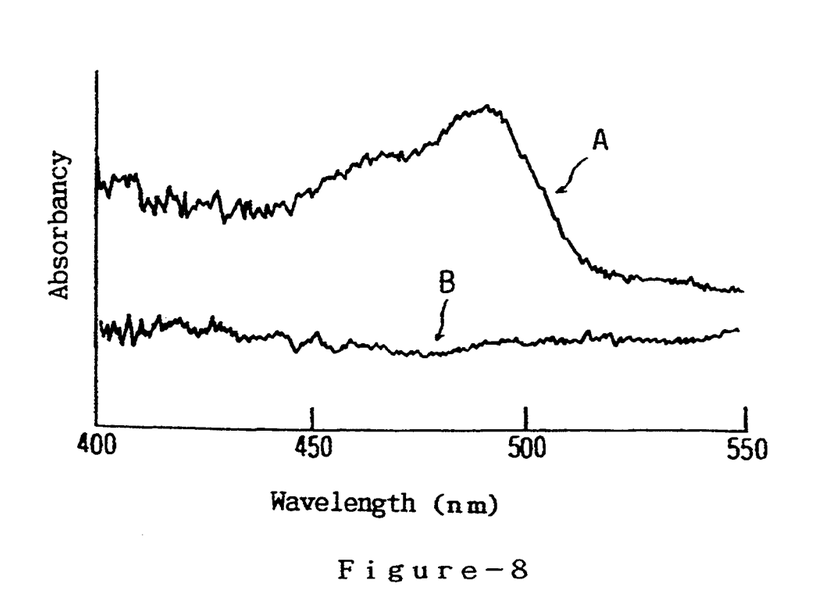
FIG. 8 is a view showing absorption spectrums of an organic chemically adsorbed film formed on a platinum electrode in an embodiment of the invention.

The absorption spectrum of the compound contained in the film was measured by a reflection method. The results of absorption spectrum are shown in FIG. 8. In FIG. 8, curve A indicates the results of OTS containing the compound while curve B shows the results of OTS without the compound. In considering molecule occupying area of the compound as 1.7 m², the number of the compound in Formula 3 is estimated to be $5.4 \times 10^{12}/cm^2$. Therefore, by washing the electrode with chloroform, $5.4 \times 10^{12}/cm^2$ holes would be made. Since the holes of OTS film formed on the platinum deposited on the glass substrate are similarly made on a platinum wire, the results of the formation of holes by the compound are applicable to the wire.

The stability of a sensor of the invention was tested by measuring dopamine, a neurotransmitter, in a bovine blood serum albumin solution—a typical protein contained in a body fluid in a large quantity—with a platinum electrode.

A test solution was prepared by dissolving 50 mM/L bovine blood serum albumin and 100 $\mu$M/L dopamine in a phosphoric acid buffer solution (0.1 M/L, pH=7.5). A three-electrode method (a platinum electrode formed with an organic thin film as a working electrode, a platinum electrode which is 10 by 10 mm square as a counter electrode and a silver/silver chloride electrode as a reference electrode) was used for measuring dopamine. A change in a cyclic voltammogram with the passage of time was measured by an electrode in a test solution, thus estimating the stability of the electrode.

Figure 9:
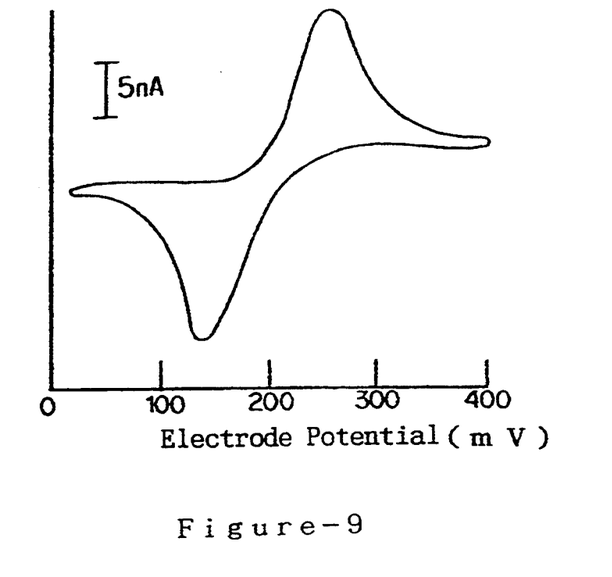
FIG. 9 is a view showing a cyclic voltammogram measured by an electrode in a test solution immediately after dipping and holding the electrode in the solution in an embodiment of the invention.
Figure 10:
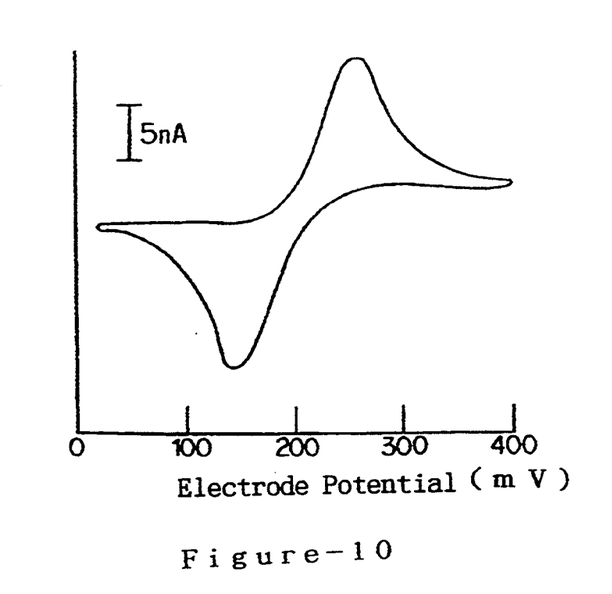
FIG. 10 is a view showing a cyclic voltammogram measured by an electrode in a test solution after dipping and holding the electrode in the test solution for twelve hours, in an embodiment of the invention.

A cyclic voltammogram measured by an electrode in a test solution immediately after dipping and holding the electrode in the solution is shown in FIG. 9, and a cyclic voltammogram of an electrode in a test solution after dipping and holding the electrode in the solution for twelve hours is shown in FIG. 10. The electrode potential unit of FIGS. 9 and 10 is mV vs. Ag/AgCl. As we can see by comparing the two figures, a change in peak current with the passage of time was within 5%, thereby indicating the capability of measuring dopamine with confidence even in a solution containing numerous proteins.

As noted above, according to an embodiment of the invention, ions were measured with confidence even in a testing solution containing numerous impurities.

Furthermore, based on this embodiment the electrode, covered with an organic monomolecular film with eighteen carbon atoms has a high water-repelling property, thereby preventing the adhesion of impurities. The film was thin enough to allow passage of ions through its holes, thus providing an ion sensor with high S/N ratio.

In this embodiment, OTS was used as a water-repelling organic thin film, but any other organic material which is water-repellent and capable of covering an electrode can be applicable. For example, $CF_3(CF_2)_8(CH_2)_2SiCl_3$ with a plurality of fluorine atoms can also be used. In addition, besides the compound in Formula 1, any compound, which is physically adsorbed to an electrode, can be applied to form holes in the film. The compound shown in Formula 4, for instance, is an example of such a compound.

As explained above, a hole dozens of angstroms in diameter can be formed on part of an organic thin film as follows:

forming a silane-based chemically adsorbed monomolecular film 2 on the surface of an electrode 1 and physically adsorbing mask compound 3 to the surface;
  washing the surface.

The ion sensor of this invention can prevent the passage of macromolecules such as proteins contained in a living body. The sensor can also be used in a solution with numerous impurities, and the device, when inserted in a living body, is useful for monitoring activities in the body. Moreover, an ion sensor of this invention can be used for properly measuring the density of ions over a long period by having its electrode covered with a water-repelling organic chemically adsorbed thin film and forming at least one hole—permitting the passage of ions and preventing the passage of biopolymers—in the film.

As noted above, the ion sensor, which has an electrode formed with a water-repelling organic chemically adsorbed thin film having holes of uniform size, does not have its electrode contaminated even in a solution with numerous impurities, thereby permitting accurate measurement of ions.

The ion sensor of the invention is also economical since its organic thin film, being covalently bonded to the electrode surface via siloxane groups (—SiO—), cannot be peeled off from the electrode and can withstand intensive usage.

The invention may be embodied in other specific forms without departing from the spirit or essential characteristics thereof. The embodiments disclosed in this application are to be considered in all respects as illustrative and not restrictive, the scope of the invention being indicated by the appended claims rather than by the foregoing description, and all changes which come within the meaning and range of equivalency of the claims are intended to be embraced therein.

I claim:

1. An ion sensor, comprising a thin film formed by fixing water-repelling chemical admolecules to the surface of an electrode via covalent bonding, wherein at least one hole having an area of 0.5–50 $nm_2$ is formed in said chemically adsorbed thin film, thereby permitting the passage of ions and preventing the passage of biopolymers.

2. The ion sensor according to claim 1, wherein said chemical admolecules are fixed to the surface of said electrode via covalent bonds comprising siloxane groups (—SiO—).

3. The ion sensor according to claim 1, wherein said chemically adsorbed film is a monomolecular film.

4. The ion sensor according to claim 1 or 3, wherein said chemically adsorbed thin film is formed on an organic siloxane-based inner layer.

5. The ion sensor according to claim 1, 3 or 4, wherein the thickness of said chemically adsorbed thin film is in the range of 1–10 nm.

6. The ion sensor according to claim 1, 3, 4 or 5, wherein the molecules of said chemically adsorbed thin film contain hydrocarbon or fluorocarbon groups.

7. The ion sensor according to claim 1, wherein the biopolymer is a protein.

8. The ion sensor according to claim 1, wherein said electrode is at least one selected from the group consisting of platinum, glassycarbon, silicon, gold and aluminum.

9. The ion sensor according to claim 1, wherein the the thin film is the product of the process comprising:

preparing a chemical adsorbent by dissolving or dispersing chemical admolecules containing water-repelling and chlorosilyl groups and mask molecules with a physical adsorption property in a nonaqueous solution;

dipping and holding an electrode having hydrophilic groups on its surface in said chemical adsorbent;

physically adsorbing the mask molecules to the surface of the electrode;

forming a chemically adsorbed film by a condensation reaction between hydrophilic groups on said electrode surface and the chlorosilyl groups of said chemical admolecules;

washing away the ureacted chemical admolecules and said mask molecules with a nonaqueous solution.

10. The ion sensor according to claim 9, wherein said mask molecule is at least one chosen from the group consisting of carbocyanin or pyridinium compounds having molecular weights in the range of 500–1000.

* * * * *